(12) United States Patent
Xiao et al.

(10) Patent No.: US 10,386,325 B2
(45) Date of Patent: Aug. 20, 2019

(54) GAS SENSOR WITH PARTITIONED FILTER

(71) Applicant: Life Safety Distribution GmbH, Hegnau (CH)

(72) Inventors: Lei Xiao, London (GB); Steven Leslie Scorfield, Zürich (CH); John Chapples, Portsmouth (GB)

(73) Assignee: LIFE SAFETY DISTRIBUTION GMBH, Hegnau (CH)

( * ) Notice: Subject to any disclaimer, the term of this patent is extended or adjusted under 35 U.S.C. 154(b) by 850 days.

(21) Appl. No.: 14/447,922

(22) Filed: Jul. 31, 2014

(65) Prior Publication Data

US 2016/0033445 A1 Feb. 4, 2016

(51) Int. Cl.
*G01N 27/40* (2006.01)
*G01N 27/404* (2006.01)
*G01N 33/00* (2006.01)

(52) U.S. Cl.
CPC .......... *G01N 27/40* (2013.01); *G01N 27/4045* (2013.01); *G01N 33/004* (2013.01); *G01N 33/0013* (2013.01); *G01N 33/0014* (2013.01)

(58) Field of Classification Search
CPC .. G01N 27/40; G01N 27/4045; G01N 33/004; G01N 33/0014; G01N 33/0013
USPC ......... 204/412, 415, 424
See application file for complete search history.

(56) References Cited

U.S. PATENT DOCUMENTS

| | | | |
|---|---|---|---|
| 4,820,386 A | 4/1989 | Laconti et al. | |
| 5,331,310 A | 7/1994 | Stetter et al. | |
| 5,338,429 A * | 8/1994 | Jolson | G01N 27/4045 204/412 |
| 5,560,810 A * | 10/1996 | Capetanopolous | G01N 33/0016 204/408 |
| 6,156,089 A * | 12/2000 | Stemmer | B01D 46/0036 55/467 |
| 6,238,467 B1 * | 5/2001 | Azarian | B01D 46/0023 360/99.17 |
| 6,399,391 B1 | 6/2002 | Tomlin | |
| 6,827,763 B2 * | 12/2004 | McGee | B01D 46/0005 55/356 |

FOREIGN PATENT DOCUMENTS

| | | |
|---|---|---|
| CN | 1113007 A | 12/1995 |
| CN | 101111767 A | 1/2008 |
| EP | 0293230 A2 | 11/1988 |
| EP | 2226627 A1 | 9/2010 |

(Continued)

OTHER PUBLICATIONS

B.S. Hobbs et al., Liquid Electrolyte Fuel Cells, Chapter 6 of Techniques and Mechanisms in Gas Sensing, 1991, pp. 161-188, published—Adam Hilger—Bristol, Philadelphia and New York.

(Continued)

*Primary Examiner* — Tamir Ayad

(74) *Attorney, Agent, or Firm* — Alston & Bird LLP

(57) ABSTRACT

A gas sensor including a housing containing a potassium permanganate element sandwiched between two polytetrafluoroethylene elements, a carbon element, a polytetrafluoroethylene element located adjacent to the carbon element, a sensing electrode, a reference electrode, and a counter electrode with attached current collectors, and an electrolyte.

20 Claims, 2 Drawing Sheets

(56) References Cited

FOREIGN PATENT DOCUMENTS

WO    2016016104 A1    2/2016

OTHER PUBLICATIONS

City Technology Limited's Product Data Sheet—7E & 7E/F CiTiceL®, Carbon Monoxide (CO) Gas Sensor, Parts Nos. 7E (AB704-400) & 7E/F (AB704-407), Mar. 3, 2014.
Europe Patent Application No. EP15739297.8, Communication pursuant to Rule 161(1) and 162 EPC, dated Mar. 7, 2017, 2 pages.
PCT Application No. PCT/EP2015/066939, International Search Report, dated Oct. 7, 2015, 4 pages.
PCT Application No. PCT/EP2015/066939, Written Opinion of the International Searching Authority, dated Oct. 7, 2015, 6 pages.
PCT Application No. PCT/EP2015/066939, International Preliminary Report on Patentability, dated Jan. 31, 2017, 7 pages.
The State Intellectual Property Office of People's Republic of China, First Office Action for Application No. 201580041672.X, dated Sep. 3, 2018, 11 pages, China.
The State Intellectual Property Office of People's Republic of China, Second Office Action for Chinese Office Application No. 201580041672.X, dated Apr. 10, 2019, 12 pages, China.

\* cited by examiner

GAS SENSOR WITH PARTITIONED FILTER

FIELD

The application pertains to gas sensors. More particularly, the application pertains to gas sensors that include a novel filter element to provide reduced cross-sensitivity to other gases and to provide longer life for the gas sensor.

BACKGROUND

Gas sensors are used in many commercial and industrial applications, including workplace monitoring for the presence of toxic or otherwise hazardous or deleterious gases and in other applications where health and safety issues require detection of specific gases in the ambient environment.

In these various applications, it is frequently necessary to monitor concentration of selected gas species down to levels of a few parts per million and less. In doing so, there is usually a need to remove, from the sampled air, other gases or volatile organic compounds that would likewise react at the sensor and generate an unwanted response. These gases normally have a myriad of different chemical properties, which therefore requires the use of a multitude of chemicals to remove each of them. For example, high surface area carbon is frequently used to adsorb most organic volatile species but the carbon is not effective at removing some of the common industrial inorganic gases. Thus, a second type of chemical must be used to remove those and so on. Typically, the carbon is coated with the second type of chemical or the two chemicals can be mixed then impregnated onto a solid support. Such an arrangement can quickly become self-destructive as the chemicals cross-react with each other, leading to decreased efficiency and longevity of the filter and gas sensor.

Gas sensors used in the foregoing applications include electrochemical gas sensors, which may operate to electrochemically reduce the gas species to be monitored. Alternatively, the gas sensor may operate by electrochemically oxidizing the target gas species sought to be detected. As a still further alternative, the electrochemical gas sensor may operate by indirect oxidation or reduction reaction of a compound that is produced in the gas sensor device involving the target gas to be detected in the monitored gaseous environment.

Electrochemical gas sensors utilize sensor cells that typically contain three electrodes—the working electrode, the reference electrode, and the counter electrode, although gas sensor cells are known having two-electrode and four-electrode structures. The electrodes are conventionally mounted within a housing that additionally contains an electrolyte, contacts, and electrical wires forming electronic circuitry of the sensor, and a gas permeable membrane that keeps the electrolyte within the cell and allows the gas to contact the measuring electrode.

Electrochemical sensor cells require an electrolyte as a component of the electrochemical cell. The electrolyte performs the transport of electrical charge between the different electrodes and therefore enables an electrical current to flow. The transport of electrical charge by the electrolyte is ionic in character rather than involving charge transport by electrons.

Conventional gas sensors contain filters that often use mixtures of chemicals to achieve multiple functionalities. Such gas sensors can have a limited lifespan due to the chemical components of the sensor reacting with each other or otherwise degrading due to environmental factors. The art therefore continues to seek improvements in electrochemical cell gas sensors. The current gas sensor comprises a novel filter that separates these materials into isolated chambers, which removes the risk of cross-reactions leading to improved overall filter efficiency and life without greatly increasing the complexity of the design.

DETAILED DESCRIPTION

Figure 1:
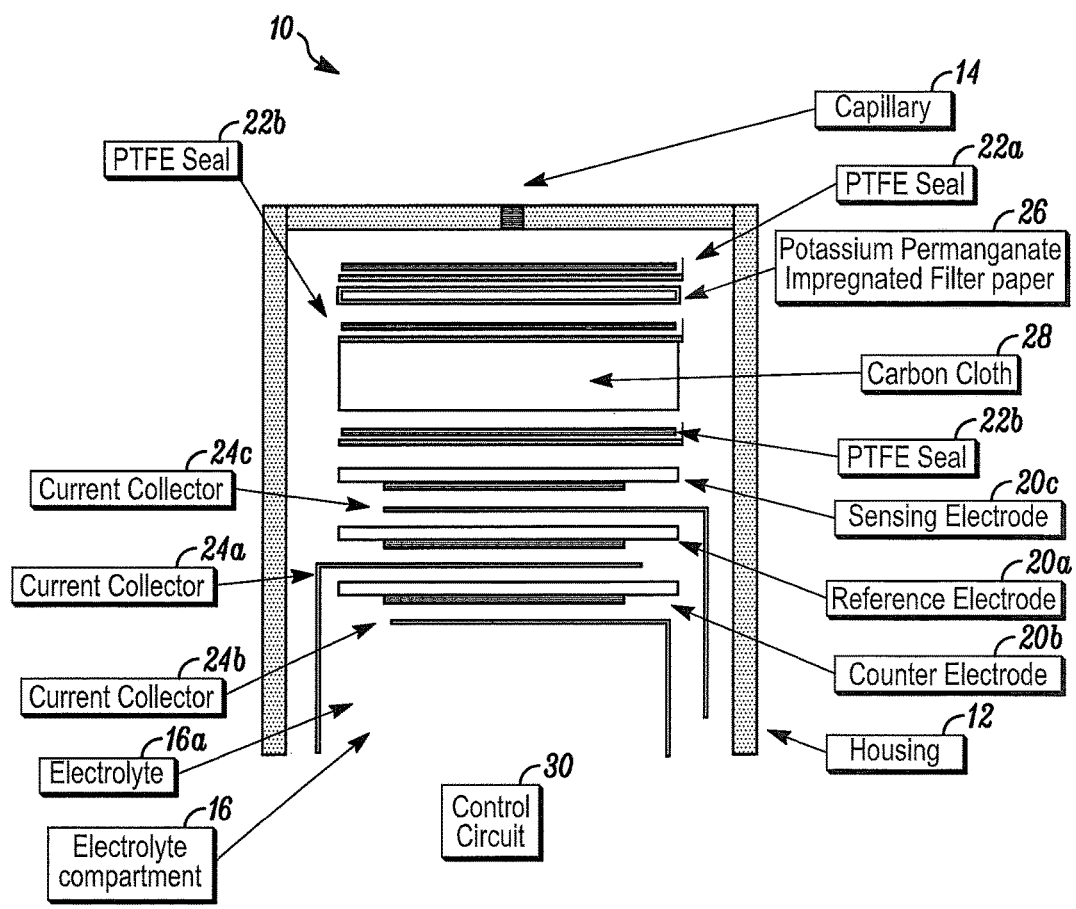
FIG. 1 is a view of a detector in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

A gas sensor having a filter that includes two or more chemicals that are incompatible or cross-reactive, which are physically separated by a gas permeable, inert barrier is described herein. FIG. 1 illustrates a gas sensor 10 in accordance herewith. It will be understood that neither the exact shape, nor the exact configuration of the sensor 10, except to the extent described below, are limitations hereof. The sensor includes a housing 12, which is formed of a relatively inert, nonconductive, gas impervious and acid resistant material. The housing can be made of ceramic, acrylonitrile butadiene styrene, polyethylene, polypropylene, polyvinylchloride, respective derivatives thereof or mixtures thereof.

Within the housing is an opening or capillary 14, through which the gas enters the housing 12. The housing can contain one or multiple openings or capillaries. Alternatively, the gas sensor can include a solid membrane sensor.

A gas permeable, inert barrier 22a, shown as "PTFE seal" in FIG. 1, can be located adjacent to the capillary 14. The gas permeable, inert barrier 22a is a solid material selected from the group consisting of fluorinated plastic, polyethylene, inorganic materials, ceramic materials, metallic foils, and mixtures thereof. One such fluorinated plastic is polytetrafluoroethylene (PTFE). Adjacent to the inert barrier 22a is a gas permeable chemical component 26, shown as "potassium permanganate impregnated filter paper" in FIG. 1, that is used to remove or degrade a gas that is present in the sample that is not the analyte of interest. For example, potassium permanganate impregnated filter paper can be used in this regard. Adjacent to the gas permeable chemical component 26 is a gas permeable, inert barrier. The inert barrier may be the same or different than inert barrier 22a. Next to the inert barrier is a second gas permeable, chemical component 28, shown as "carbon cloth" in FIG. 1. A gas permeable, inert barrier 22b, shown as "PTFE seal" in FIG. 1, can be located next to the second chemical component 28. A number of materials could, in principle, be used as the inert barrier provided that they meet the criteria of being chemically inert and possess sufficient porosity so as not to significantly restrict gas flow through the filter compartment. Also, a physical porous separator can be used when combinations of the filter material include one component that is a strong oxidant that is capable of oxidizing the other filter component, or a strong reducing agent that is capable of reducing the other filter component, or an acidic filter component and a basic filter component.

The interior volume of the housing includes an electrolyte compartment 16 containing an electrolyte 16a, and an electrode assembly including a counter electrode 20b, a reference electrode 20a and a sensing electrode 20c. The electrolyte can be sulfuric acid. The sensing electrode 20c can be adjacent to the inert barrier 22b and a current collector 24c. The reference electrode 20a is adjacent to the current collector 24c and the counterelectrode 20b. The current collector 24a is adjacent to the counter electrode 20b.

A control circuit 30 is connected to the housing and controls the sensor. Alternatively, the control center can be separated from the housing. The control circuit refers to the external circuit, which might be a potentiostat or a simple load resistor plus downstream signal acquisition and display hardware.

The gas sensor can operate in a diffusion mode or in an in-line mode, and includes a gas inlet and gas outlet.

EXAMPLE 1

Figure 2:
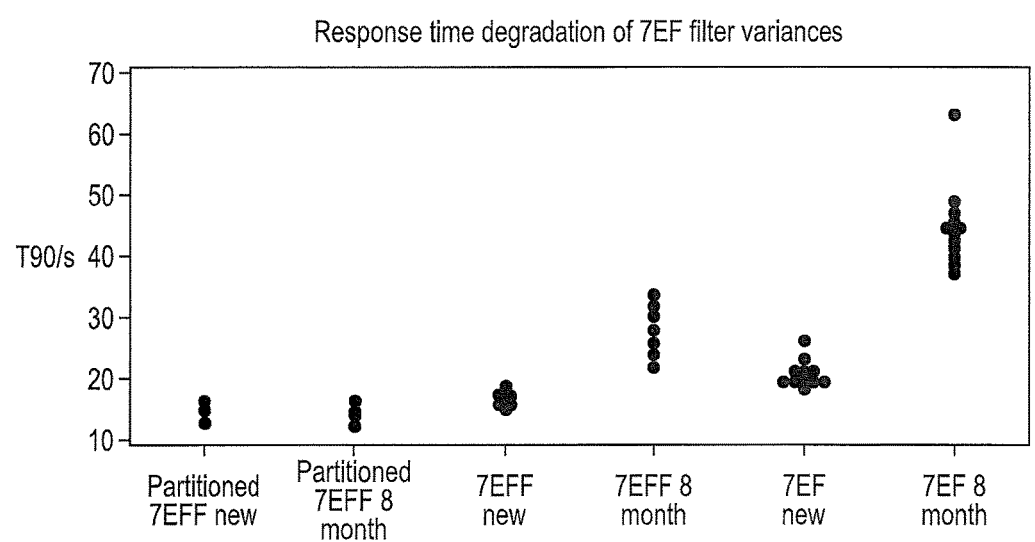
FIG. 2 is a view of a graph detailing results of longevity of various gas detectors.

Several different gas sensors were exposed to 5 minutes of air, followed by 5 minutes of 200 ppm carbon monoxide (CO), followed by 5 minutes of air, then the detection capacity of the sensors for carbon monoxide was noted. The T90 is calculated as the time taken to for the sensor's output to reach 90% when stabilized in 200 ppm CO (response after 5 minutes). The graph of FIG. 2 shows the T90 of three different CO gas sensors, namely 7EF, 7E/F and the claimed gas sensor (partitioned 7EFF) when those gas sensors were new as compared to those sensors after 8 months of use. (The 7E and 7E/F are electrochemical CO sensors manufactured by City Technology Ltd, UK.) The graph shows that there is very little if any change in the claimed gas sensor after 8 months of use whereas the other gas sensors show changes in response times after 8 months of use. Thus, the claimed gas sensor has a longer life than currently available gas sensors.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:
1. A gas sensor comprising:
a housing;
an opening in the housing;
a plurality of electrodes disposed within the housing;
a filter disposed within the housing between the opening and the plurality of electrodes, wherein the filter comprises two or more chemicals that are cross-reactive; and
a barrier disposed between at least two of the two or more chemicals within the filter, wherein the barrier is a gas permeable, inert barrier.
2. The gas sensor of claim 1, wherein the gas permeable, inert barrier comprises a solid material selected from the group consisting of fluorinated plastic, polyethylene, inorganic materials, ceramic materials, metallic foils, and mixtures thereof.
3. The gas sensor of claim 1, wherein the gas permeable, inert barrier comprises polytetrafluoroethylene.
4. The gas sensor of claim 1, wherein one of the two or more chemicals comprises carbon.
5. The gas sensor of claim 1, wherein one of the two or more chemicals comprises potassium permanganate.
6. The gas sensor of claim 1, wherein a first chemical of the two or more chemicals comprises carbon, and wherein a second chemical of the two or more chemicals comprises potassium permanganate.
7. The gas sensor of claim 1, wherein the gas permeable, inert barrier comprises polytetrafluoroethylene, wherein at least a first Chemical of the two or more chemicals comprises carbon, and wherein at least a second chemical of the two or more chemicals comprises potassium permanganate.
8. The gas sensor of claim 1, wherein the housing comprises an inert, gas impervious material.
9. The gas sensor of claim 8, wherein the housing comprises acrylonitrile butadiene styrene.
10. The gas sensor of claim 1, further comprising an electrolyte disposed within the housing.
11. The gas sensor of claim 10, wherein the electrolyte is sulfuric acid.
12. A gas sensor comprising:
a housing;
a potassium permanganate element sandwiched between two polytetrafluoroethylene elements;
a carbon element sandwiched between two polytetrafluoroethylene elements, wherein the potassium permanganate element is physically separated from the carbon element by at least one polytetrafluoroethylene element, and wherein the at least one polytetrafluoroethylene element is a gas permeable, inert barrier;
a sensing electrode;
a reference electrode;
a counter electrode with attached current collectors; and
an electrolyte.
13. The gas sensor of claim 12, wherein the housing comprises acrylonitrile butadiene styrene.
14. The gas sensor of claim 12, wherein the electrolyte comprises sulfuric acid.
15. The gas sensor of claim 12, further comprising a gas comprising carbon monoxide, wherein the potassium permanganate element and the carbon element are configured to allow carbon monoxide to pass through.
16. The gas sensor of claim 1, wherein at least one of the two or more chemicals comprises potassium permanganate impregnated filter paper.
17. The gas sensor of claim 1, wherein at least one of the two or more chemicals comprises a carbon cloth.
18. The gas sensor of claim 1, wherein the filter comprises: a second inert barrier disposed between the opening and the two or more chemicals, and a third inert barrier between the two or more chemicals and the plurality of electrodes.
19. The gas sensor of claim 12, Wherein the potassium permanganate element is disposed between an opening in the housing and the carbon element, and wherein the carbon element is disposed between the potassium permanganate element and any of the sensing electrode, the reference electrode, or the counter electrode.

20. The gas sensor of claim 12, wherein the housing comprises at least one of: one or more openings, or a solid membrane.

\* \* \* \* \*